United States Patent
Gross et al.

(10) Patent No.: US 11,631,485 B2
(45) Date of Patent: Apr. 18, 2023

(54) SYSTEM AND METHOD FOR JOINT CLINICAL DECISION FOR PHARMACEUTICALS

(71) Applicant: KONINKLIJKE PHILIPS N.V., Eindhoven (NL)

(72) Inventors: Brian David Gross, North Andover, MA (US); Ivan Salgo, Pelham, MA (US); Andrew Franklin Arthur, Hollis, NH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/648,692

(22) PCT Filed: Sep. 25, 2018

(86) PCT No.: PCT/EP2018/075903
§ 371 (c)(1),
(2) Date: Mar. 19, 2020

(87) PCT Pub. No.: WO2019/063520
PCT Pub. Date: Apr. 4, 2019

(65) Prior Publication Data
US 2020/0286608 A1    Sep. 10, 2020

Related U.S. Application Data

(60) Provisional application No. 62/563,119, filed on Sep. 26, 2017.

(51) Int. Cl.
*G16H 20/13* (2018.01)
*G16H 20/40* (2018.01)
(Continued)

(52) U.S. Cl.
CPC ............. *G16H 20/13* (2018.01); *G16H 20/30* (2018.01); *G16H 20/40* (2018.01); *G16H 50/20* (2018.01)

(58) Field of Classification Search
CPC ........ G16H 20/30; G16H 10/60; G16H 15/00; G16H 20/40; G16H 20/13
(Continued)

(56) References Cited

U.S. PATENT DOCUMENTS

| 8,838,395 B2 | 9/2014 | Matsiev et al. |
| 2006/0047538 A1* | 3/2006 | Condurso ............... G16H 70/40 705/3 |

(Continued)

FOREIGN PATENT DOCUMENTS

| EP | 2059300 B1 * | 10/2017 | ......... A61B 5/04085 |
| WO | WO-2014186387 A1 * | 11/2014 | ............. G16H 50/50 |
| WO | 2017051271 A1 | 3/2017 | |

OTHER PUBLICATIONS

Heitjan DF. Ignorability and coarse data: some biomedical examples. Biometrics. Dec. 1993;49(4):1099-109. PMID: 8117903. (Year: 1993).*

(Continued)

*Primary Examiner* — Hiep V Nguyen (57) ABSTRACT

A clinical therapy system (10) includes a drug delivery device (14) configured to delivery medication to a patient. One or more therapy devices (12, 16, 11, 13, 15, 17) are configured to provide therapy or to monitor the patient. A computer (70) is programmed to perform a CDS method (100) including: receiving clinical context data for the patient from a health information system (HIS) (18); receiving high fidelity data (20, 22, 24, 60, 62, 64, 66) comprising real time measurements for the patient from one or more of the drug delivery device, one or more vital sign sensors, and at least one device of the one or more therapy devices;

(Continued)

applying one or more physiologic models (30, 32, 34 36, 38) to the combination of the clinical context data and the high fidelity data to generate a clinical prediction for the patient; outputting a therapy recommendation for the patient based on the clinical prediction for the patient; and controlling operation of the drug delivery device or one of the therapy devices based on the therapy recommendation.

16 Claims, 3 Drawing Sheets

(51) Int. Cl.
    *G16H 20/30*     (2018.01)
    *G16H 50/20*     (2018.01)

(58) Field of Classification Search
    USPC .............................................................. 705/3
    See application file for complete search history.

(56) References Cited

U.S. PATENT DOCUMENTS

| | | | |
|---|---|---|---|
| 2006/0149144 A1* | 7/2006 | Lynn | G16H 50/20 |
| | | | 600/323 |
| 2013/0231947 A1* | 9/2013 | Shusterman | G16H 40/67 |
| | | | 705/2 |
| 2013/0325035 A1 | 12/2013 | Hauck et al. | |
| 2017/0095670 A1 | 4/2017 | Ghaffari et al. | |
| 2017/0127993 A1* | 5/2017 | Olivier | A61B 5/6823 |

OTHER PUBLICATIONS

Daniel Heitjan and Donald B. Rubin; Ignorability and coarse data; The Annals of Statistic; 1991, vol. 19, No. 4, 2244-2253 (Year: 1991).*

"Acute Respiratory Distress Syndrome—The Berlin Definition"; JAMA, 2012, 307(23), pp. 2526-2533.

PCT/EP2018/075903 ISR & WO, dated Jan. 2, 2019, 15 Page Document.

* cited by examiner

FIG. 3

SYSTEM AND METHOD FOR JOINT CLINICAL DECISION FOR PHARMACEUTICALS

CROSS-REFERENCE TO PRIOR APPLICATIONS

This application is the U.S. National Phase application under 35 U.S.C. § 371 of International Application No. PCT/EP2018/075903, filed on Sep. 25, 2018, which claims the benefit of U.S. Provisional Patent Application No. 62/563,119, filed on Sep. 26, 2017. These applications are hereby incorporated by reference herein.

FIELD

The following relates generally to the medical care arts, medical therapy delivery arts, clinical decision support arts, and to related arts.

BACKGROUND

Some existing medication delivery systems deliver administration of medications with closed loop control of the dosage or rate of drug delivery. Examples include insulin pumps delivering insulin controlled to a set glucose level based on glucose sensor input, and an infusion pump delivering a vasopressor controlled for a targeted blood pressure. These systems leverage real-time data to control medication delivery. Clinical decision support systems also exist which can provide a clinical recommendation for initiating or modifying a medication therapy if clinical conditions are detected for which they transact on, in some instances including a drug therapy recommendation. In some examples, analytics may be used to determine which patients are best served by a given medication.

Some existing systems provide a recommendation if clinical conditions can be detected for which they transact on. Such systems are commonly referred to as clinical decision support (CDS) systems. The CDS recommendation may, in some instances, include a drug therapy recommendation, e.g. a recommendation to initiate vasopressor therapy. However, existing CDS systems rely upon data in the health information systems (HIS). The contents of the HIS are entered by clinicians, which has the advantage of ensuring the entered data is validated by the clinician and succinctly summarizes relevant medical information. However, this entry approach introduces substantial delay such that the contents of the HIS have a substantial time lag and are not up-to-date. Moreover, the clinician-entered HIS data are generally summaries or occasional updates, and have low fidelity, that is, low sampling frequency.

The following discloses a new and improved systems and methods.

SUMMARY

In one disclosed aspect, a clinical therapy system includes a drug delivery device configured to delivery medication to a patient. One or more therapy devices are configured to provide therapy or to monitor the patient. A computer is programmed to perform a CDS method including: receiving clinical context data for the patient from a health information system (HIS); receiving high fidelity data comprising real time measurements for the patient from one or more of the drug delivery device, one or more vital sign sensors, and at least one device of the one or more therapy devices; generating a clinical prediction for the patient from a combination of the clinical context data and the high fidelity data to; outputting a therapy recommendation for the patient based on the clinical prediction for the patient; and controlling operation of the drug delivery device or one of the therapy devices based on the therapy recommendation.

In another disclosed aspect, a non-transitory computer readable medium stores instructions executable by at least one electronic processor to perform a clinical decision support method comprising: receiving clinical context data for a patient from a health information system (HIS); receiving high fidelity data comprising real time measurements for the patient from one or more of a drug delivery device, one or more vital sign sensors, and at least one device of one or more therapy devices; applying one or more physiologic models to the combination of the clinical context data and the high fidelity data to generate a clinical prediction for the patient; outputting a therapy recommendation for the patient based on the clinical prediction for the patient; and controlling operation of the drug delivery device or one of the therapy devices based on the therapy recommendation.

In another disclosed aspect, a clinical therapy system includes a drug delivery device configured to delivery medication to a patient. A plurality of therapy devices is configured to provide therapy or to monitor the patient. The therapy devices include a ventilator, a patient monitor, a fluid regulatory device, a cooling blanket, a ventricular assist device, and a mechanically adjustable patient bed. A computer includes a local computer and a cloud computing resource. The computer is programmed to perform a CDS method including: with the local computer, receiving clinical context data for the patient from a health information system (HIS); with the local computer, receiving high fidelity data comprising real time measurements for the patient from one or more of the drug delivery device, one or more vital sign sensors, and at least one device of the one or more therapy devices; with the cloud computing resource, applying one or more physiologic models to the combination of the clinical context data and the high fidelity data to generate a clinical prediction for the patient; outputting a therapy recommendation for the patient based on the clinical prediction for the patient; and controlling operation of the drug delivery device or one of the therapy devices based on the therapy recommendation.

One advantage resides in providing more timely clinical support recommendation for a patient by leveraging, in addition to context data obtained from the HIS, high fidelity data obtained from one or more medical devices providing therapy or one or more drug delivery devices for or monitoring of a patient.

Another advantage resides in employing such clinical support to provide closed loop control of a therapy device delivering therapy to a patient.

Another advantage resides in providing the foregoing benefits in the context of ventilator therapy provided for the patient.

Another advantage resides in providing the foregoing benefits in the context of a medication delivery device providing a medication to the patient.

Another advantage resides in providing controlled delivery of a vasopressor to a patient.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

It is recognized herein that existing approaches for closed loop drug delivery control are of limited utility because they do not take into account the complexity of human physiology. For example, an insulin pump delivering glucose at a level based on glucose sensor input does not take into account the physiological basis for a change in the glucose level detected by the glucose sensor. Depending upon this physiological basis, it may, or may not, be appropriate for the insulin pump to adjust the level of the glucose delivery. Likewise, an infusion pump delivering vasopressor at a level controlled by measured blood pressure does not take into account the physiological basis for a detected change in measured blood pressure. Again, depending upon this physiological basis, it may, or may not, be appropriate for the infusion pump to adjust the level of the vasopressor delivery.

Embodiments disclosed herein comprise a system and method for clinical decision support (CDS) to improve pharmaceutical effectiveness and safety by providing recommendations to the care team, patient, or control signals to external devices including drug delivery device and other intervention and therapy devices. Recommendations for pharmaceuticals include dosing and timing of the drug, as well as other direct therapy and control signals for other interventions such as ventilator management. Some embodiments disclose a system facilitation or optimization of the care processes around the administration of a given pharmaceutical. By operating with real-time data, with clinical context from the health information systems (HIS), and through control signals to therapeutic devices pharmacological therapy can be implemented. In one embodiment, this can be optimized.

Critical cardiac, pulmonary, or cardiopulmonary care situations can be treated by pharmaceutical intervention, therapy intervention, or a combination of these. The disclosed electronic Clinical Decision Support (CDS) system synergistically generates both drug delivery and therapy device control. This recognizes that the balance between the pharmaceutical and therapy treatment pathways are best determined concurrently. For example, fluid regulation can be achieved by therapy, e.g. intravenous (IV) fluid delivery or withdrawal, or by use of a pharmaceutical such as the loop diuretic Lasix® (Furosemide), or by a combination of these. As another example, respiratory assistance can be provided by a mechanical ventilator and/or by various drugs that operate to open the airway.

The disclosed electronic CDS system receives as inputs the current pharmaceutical prescription (drug, delivery route, and dosage) and current therapy settings for mechanical ventilation (e.g. mode, pressure, volume, gas mix, flow pattern settings), thermal regulation via cooling blanket, internal thermal control catheter, or external blood cooling, fluid balance by way of IV fluid delivery, cardiac support by way of a ventricular assist device, patient position by way of a mechanically adjustable hospital bed, or so forth; as well as additional information such as current vital signs and clinical assessments.

The electronic CDS includes at least one physiologic model (e.g. a cardiovascular model) and a manually authored preferred care process for a particular drug, and optionally additional clinical models such as machine learned empirical models. These inputs are used to compute the optimal drug dose and therapy settings for a given patient. In a preferred embodiment, control signals may be sent to an infusion pump or other drug delivery device, and to a mechanical ventilator, fluid regulatory device, a cooling blanket, a mechanically-adjustable hospital bed controller, ventricular assist device controller, cardiac pacemaker or other therapy device to automatically implement some or all settings. Additionally or alternatively, one or more optimized settings may be communicated to medical personnel as natural language recommendation(s), e.g. as text displayed on a display. By jointly optimizing both drug delivery and therapy settings, more optimal pharmacotherapy is achievable.

Figure 1:
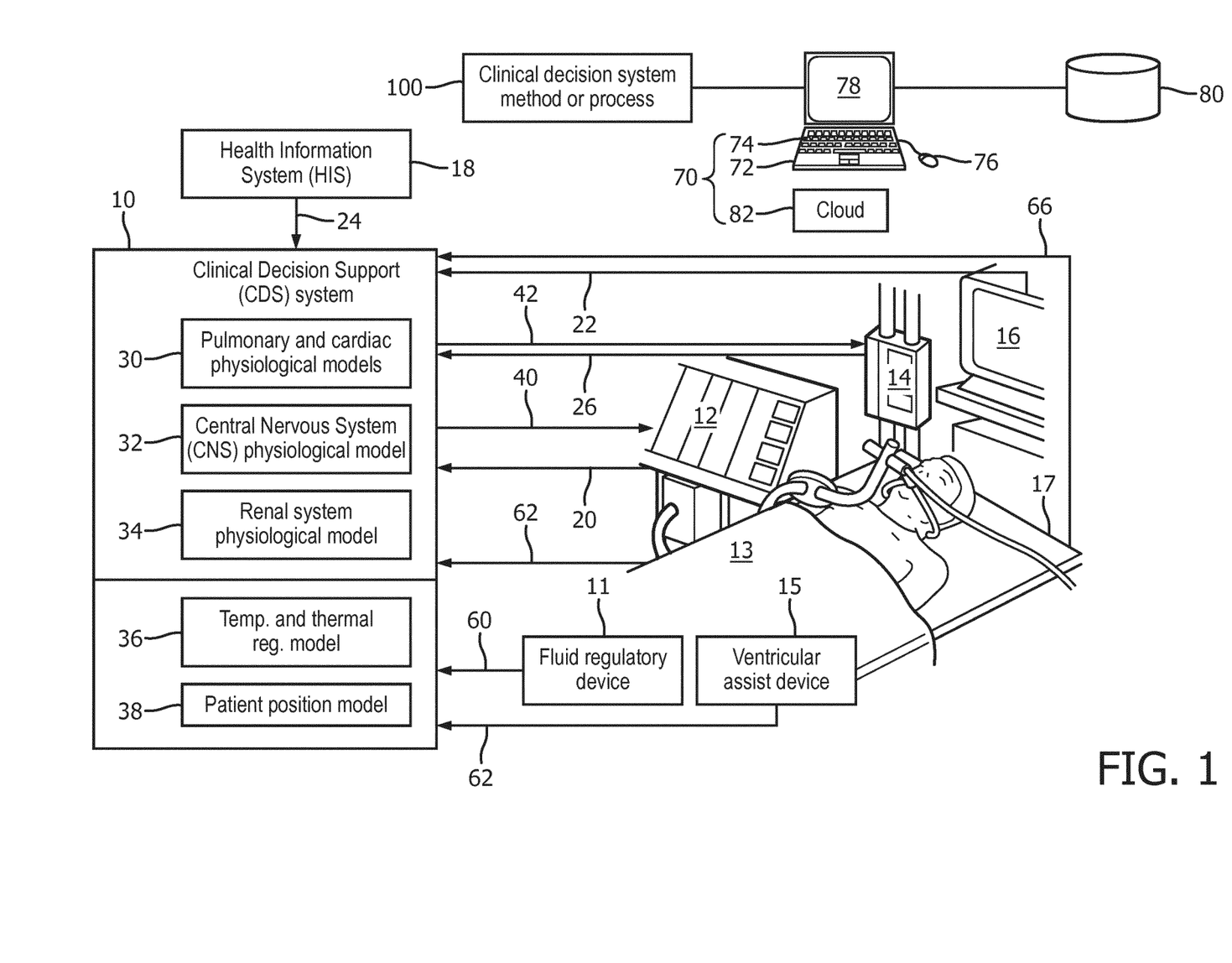
FIG. 1 diagrammatically illustrates a therapy delivery system including one or more drug delivery devices, one or more therapy devices, and a clinical decision support (CDS) system as disclosed herein.

With reference to FIG. 1, an illustrative embodiment comprises a clinical decision support (CDS) or therapy system 10. In one embodiment, the CDS system 10 is implemented as a collection of rules operating on the Clinical Analytics Platform (e.g. the Philips HealthSuite Digital Platform implemented on a cloud computing resource) taking non-validated or raw data from devices and monitors (e.g. an illustrative ventilator 12, an illustrative drug delivery device such as an infusion pump 14 (or, alternatively, a cooling device, a ventilator system, a defibrillator system, a patient bed, and so forth), and an illustrative patient monitor 16; or other example shown schematically, such as a fluid regulatory device 11, a cooling blanket 13, a ventricular assist device 15, and a mechanically-adjustable patient hospital bed 17; these are merely non-limiting illustrative examples), and clinical data from available electronic health information systems, diagrammatically indicated in FIG. 1 by an illustrative electronic health information system (HIS) 18. More generally, the HIS 18 may include, by way of non-limiting illustration, a general HIS, a cardiovascular information system (CVIS), Picture Archiving and Communication System (PACS), radiology information system (RIS), and/or other domain-specific HIS, and/or so forth.

In an embodiment, the CDS system 10 receives afferent signals by which it acquires clinical context, such as temporal hierarchical multi-resolution analysis and decomposition of both time and location data. Examples for device afferent signals may include pressure, volume and FIO2 data, pulse pressure variability, vent pressure and vent flow waveforms 20 coming out of the ventilator 12. Afferent signals 22 from the patient monitor 16 may include ECG, pulse wave time of flight, blood pressure (systemic, CVP, and/or PA), and a capnogram (e.g., to model dead space in the lungs). Afferent signals 24 from the HIS 18 include laboratory data such as arterial blood gas (ABG), Micro biology results, clinical assessments, procedure reports, radiology and imaging results. Although not used in this example, afferent signals 26 from the infusion pump 14 may, for example, include an infusion flow rate and possibly an identification of the medication being administered by the infusion pump 14. In addition, each of the devices illustrated in FIG. 1 (e.g., the fluid regulatory device 11, a cooling blanket 13, a ventricular assist device 15, and a mechanically-adjustable patient hospital bed 17) can generate similar corresponding afferent signals 60, 62, 64, and 66.

The afferent signals 20, 22, 24, 60, 62, 64, 66 comprise high fidelity data (e.g. real time measurements from the corresponding devices). This high fidelity data enables the CDS system 10 to rapidly detect deterioration of patient condition. On the other hand, the high fidelity data is "raw" data in the sense that it has not been reviewed and/or analysed by a doctor or other medical personnel. By contrast, data received from the HIS 18 are not of high fidelity. For example, patient condition information recorded by a doctor or nurse are acquired only when the patient is examined by the doctor or nurse, and such data only enter the HIS 18 when a human being (e.g. doctor or nurse) enters the data into the HIS 18. This means reliance on HIS data exclusively can introduce significant delays in appropriate treatment such as medication selection, dosing, intervention timing, e.g. vent settings, IV infusion and ventilators cardiac and pulmonary. On the other hand, the data stored in the HIS 18 is usually reviewed prior to or during entry, and may include or encapsulate results of an analysis performed by a doctor or other qualified medical person.

The disclosed approach leverages both high fidelity data provided to the CDS system as afferent signals and also data retrieved from the HIS 18. This provides the benefits of review/analysis captured in the HIS data together with timeliness provided by the high fidelity data, in order to provide time-critical joint optimization of both drug delivery and (non-drug) therapy delivery.

At the CDS system 10, the acquired afferent signals are used to create a series of physiological models 30, 32, 34 36, 38 which produce predictions as to the interaction between systems (e.g. pulmonary and cardiac). For example, by analysing the ECG, pulse wave time of flight, blood pressure (systemic, CVP, and PA), pulse pressure variability, vent pressure and vent flow waveforms, capnogram (to model dead space), and by modulating where the vent initiates a brief plateau pressure, and by recording the resulting pressure stabilization value and time constant, pulmonary mechanics and cardiovascular fluid status. From these data sets, the pulmonary and cardiac physiological models 30 can be derived to predict impact to cardiac output and oxygen delivery (e.g. delivery pressure, flow, and gas constituency settings for the ventilator 12. Based on these inputs, the model 30 predicts optimal input pressure, flow and gas constituency settings, as well as fluid responsiveness to hemodynamic volume challenges. Such a model can be constructed from application of existing clinical knowledge such as reduction of care heuristics extracted from subject matter experts, or constructed through previously unknown relationships of physiology and therapy options discovered through application of machine learning or deep learning technologies on large data sets.

Through these models 30, 32, 34, 36, 38 not only can therapy be planned an optimized, but overall multi-organ status can be derived and a risk score of worsening cardiopulmonary status. The same can be achieved with renal, CNS, and the rest of the body systems (e.g. CNS physiological model 32, renal system physiological model 34, a patient temperature and thermal regulation model 36, a patient position model 38) based on their afferent signals. An example of this can be seen when an acute kidney injury score (AKIN) is generated when a medication known to cause kidney injury such that the medication dose can be modified if kidney injury is detected by the score. Further a site implemented early warning scoring program where once a risk score changes for the worst, the operator is instructed to administer oxygen and summoned the rapid response team In some examples, the CDS system 10 includes a computer system 70 configured to process the efferent signals 20, 22, 24, 60, 62, 64, 66 and the models 30, 32, 34. The computer system 70 includes a local computer 72 (i.e., a workstation a computer or workstation or other electronic data processing device with typical components, such as at least one electronic processor 74, at least one user input device (e.g., a mouse, a keyboard, a trackball, and/or the like) 76, and a display device 78. In some embodiments, the display device 78 can be a separate component from the computer 72. The workstation 72 can also include one or more databases 80 (stored in a non-transitory storage medium such as RAM or ROM, a magnetic disk, or so forth), and/or the workstation can be in electronic communication with one or more databases (e.g., the HIS 18). The computer system 70 also includes a cloud computing resource 82 (e.g., a server).

The computer 72 and the cloud computing server 82 are operatively connected with a non-transitory storage medium (not shown) that stores instructions which are readable and executable by the at least one electronic processor 20 to perform disclosed operations including performing a CDS method 100. The non-transitory storage medium may, for example, comprise a hard disk drive, RAID, or other magnetic storage medium; a solid state drive, flash drive, electronically erasable read-only memory (EEROM) or other electronic memory; an optical disk or other optical storage; various combinations thereof; or so forth.

The CDS system 10 may output direct therapy and control signals for other interventions such as ventilator management. Thus, for example, an efferent control signal 40 may be output from the CDS system 10 to the ventilator 12 to set the ventilation mode and/or settings of the ventilation (e.g. setting optimal input pressure, flow and gas constituency settings, e.g. FIO2, for the ventilator 12). Likewise, an efferent control signal 42 may be output from the CDS system 10 to the infusion pump 14 to set infusion pump settings such as vasopressor infusion rate.

Figure 2:
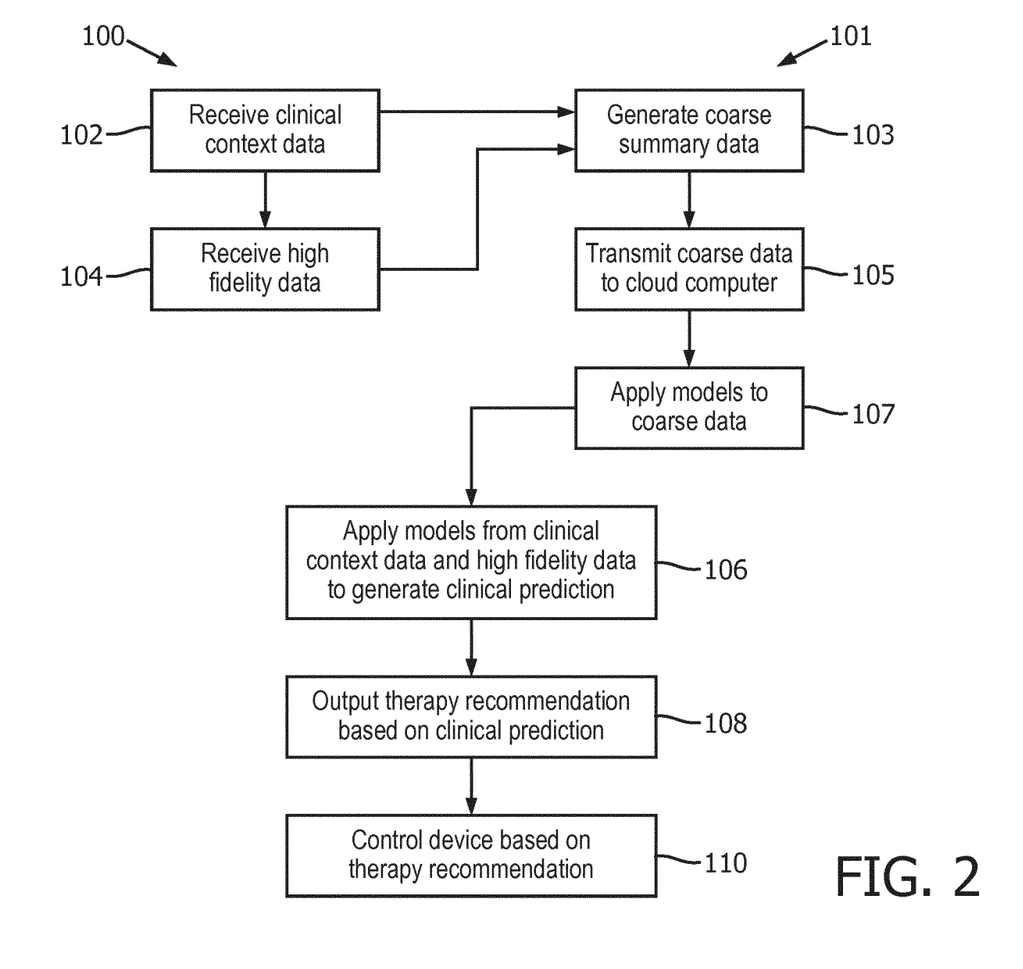
FIG. 2 shows an exemplary flow chart operation of the system of FIG. 1.

With reference to FIG. 2, an illustrative embodiment of the CDS method 100 is diagrammatically shown as a flowchart. At 102, the computer system 70 is configured to receive clinical context data for the patient from the HIS 18. At 104, the computer system 70 is configured to receive high fidelity data (i.e., the afferent signals 20, 22, 24, 60, 62, 64, 66) comprising real time measurements for the patient from one or more of the drug delivery device 14, one or more vital sign sensors, and at least one device of the one or more therapy devices 12, 16, 11, 13, 15, 17. The high fidelity data can include, for example, one or more of gas pressure, volume and FiO2 settings for the ventilator 12, fluid regulatory data for the fluid regulatory device 11, patient temperature and thermal regulation data for the cooling blanket 13, cardiac support data from the ventricular assist device 15, and patient position data from the mechanically adjustable patient bed 17.

At 106, a clinical prediction for the patient is generated from a combination of the clinical context data and the high fidelity data. To do so, one or more of the physiologic models 30, 32, 34, 36, 38 are applied to the combination of the clinical context data and the high fidelity data to generate a clinical prediction for the patient. A CDS data processing method 101 may be used, which includes operations 103-107. The processing implementing the physiologic models can be computationally complex, and may be advantageously performed using a high-capacity computing resource such as the computing server 82 (e.g. a cloud computing resource or other multi-computer computing resource). On the other hand, transmitting the high fidelity data in raw form to the computing server 82 may be a high bandwidth proposition. Accordingly, in some embodiments, preprocessing of the high fidelity data is performed at the local computer 72 to reduce the bandwidth requirement while still leveraging the high-capacity computing resource 82 for the complex physiological model(s) processing. For example, in operation 103, the local computer 72 is configured to process the high fidelity data 20, 22, 24, 60, 62, 64, 66 to generate course summary data at a coarser resolution then the high fidelity data. At 105, the course summary data is transmitted or communicated to the cloud computing server 82. By way of illustration, heart rate data sampled at a millisecond-level rate may be processed at 103 to generate average, minimum, and maximum heart rate values for larger time blocks (e.g. five minute time blocks) and only the average, minimum, and maximum heart rate values are then transmitted to the computing server 82 at operation 105. At 107, the cloud computing server 82 applies the one or more physiological models 30, 32, 34, 36, 38 to the combination of the clinical context data and the high fidelity data represented by the coarse summary data.

In other examples, when the therapy device includes the ventilator 12, the applying includes applying pulmonary and cardiac physiologic models 30 to the combination of the clinical context data and the high fidelity data including the ventilator data to generate the clinical prediction for the patient. Similarly, when the therapy device includes the fluid regulatory device 11, the applying includes applying fluid and renal models 34 to the combination of the clinical context data and the high fidelity data including the fluid regulatory data to generate the clinical prediction (e.g., intravenous fluid delivery dose amount and delivery rate) for the patient. When the therapy device includes the cooling blanket 13, the applying includes applying the patient temperature and thermal regulation model 36 to the combination of the clinical context data and the high fidelity data including the patient temperature and thermal regulation data to generate the clinical prediction for the patient. When the therapy device includes the ventricular assist device 15, the applying includes applying the cardiac support model 30 to the combination of the clinical context data and the high fidelity data including the cardiac support data to generate the clinical prediction for the patient. When the therapy device includes the mechanically adjustable patient bed 17, the applying includes applying the patient position model 38 to the combination of the clinical context data and the high fidelity data including the patient position data to generate the clinical prediction for the patient.

At 108, the computer system 70 is configured to output a therapy recommendation 40, 42 based on the clinical prediction for the patient generated at 106. At 110, the computer system 70 is configured to control operation of the drug delivery device 14 or one of the therapy devices 12, 16, 11, 13, 15, 17 based on the therapy recommendation. For example, the controlling can include increasing or decreasing an amount of pressure, flow and gas constituency settings from the ventilator 12 delivered to the patient and increasing or decreasing an amount of a respiratory drug delivered to the patient by the drug delivery device 14. In another example, the controlling includes increasing or decreasing an amount of dose or a delivery rate from the fluid regulatory device 11 delivered to the patient and increasing or decreasing an amount of a respiratory regulatory drug delivered to the patient by the drug delivery device 14. In another example, the controlling includes increasing or decreasing an amount of heat delivered to the patient from the cooling blanket 13. In another example, the controlling includes increasing or decreasing a speed of the ventricular assist device 15. In another example, the controlling includes moving a portion of the mechanically adjustable patient bed 17 to adjust a position of the patient. Another example is using the Berlin criteria for grading acute respiratory distress syndrome (ARDS), as criteria to initiate movement of the patient into a prone position, or initiating inhalation of nitric oxide to promote oxygenation (Acute Respiratory Distress Syndrome—The Berlin Definition, JAMA. 2012; 307(23):2526-2533).

Figure 3:
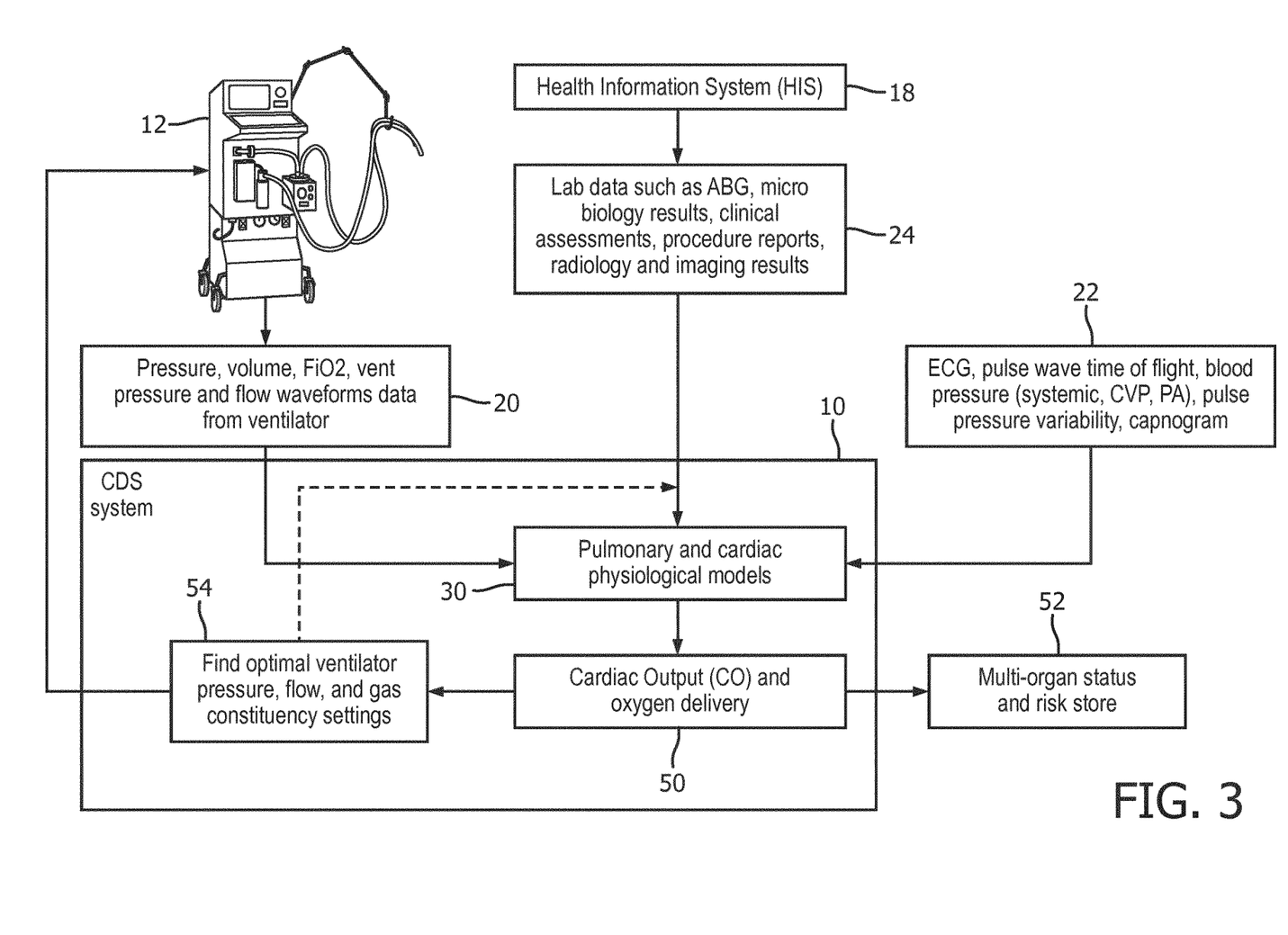
FIG. 3 diagrammatically illustrates an application of the CDS system of FIG. 1 for optimizing ventilator settings.

With reference to FIG. 3, an illustrative application of the CDS system 10 of FIG. 1 for optimizing ventilator settings is described. For this application, the CDS system 10 receives afferent signals including: pressure, volume, FiO2, and vent pressure and flow waveforms data 20 from ventilator 12; vital sign data such as ECG, pulse wave time of flight, blood pressure (systemic, CVP, PA), pulse pressure variability, and/or capnogram data from the patient monitor 16; and lab data 24 from the HIS 18 such as ABG, Micro biology results, clinical assessments, procedure reports, radiology and imaging results. These data are used to create the pulmonary and cardiac physiological models 30 for the specific patient. The pulmonary and cardiac physiological models 30 are used to predict salient patient parameters 50 such as, in this illustrative application, cardiac output and oxygen delivery. An example is demonstrated by implementing well know relationship between the partial pressure of CO2 and the minute ventilation (e.g., tidal volume multiplied by ventilator rate) administered to a patient not breathing on their own. These calculated patient parameters 50 may be used to provide a real-time assessment of multi-organ status and a risk score 52. Additionally, in an operation 54 controlled device parameters such as ventilator pressure, flow, and gas constituency (e.g. FiO2) settings may be adjusted iteratively, using the model 30 to predict the impact of the device parameter adjustments, so as to optimize the device parameters. In the illustrative case, the thusly optimized ventilator pressure, flow, and FiO2 settings are an efferent signal output by the CDS device 10 to the ventilator 12 to control the ventilation therapy provided by the ventilator 12.

In the following, some other illustrative examples of applications of the CDS system 10 are described. In one embodiment, the CDS system 10 is applied to predict medications related health improvement in cases where the medications have narrow ranges of physiologic impact such as renal function or liver function. In another embodiment, efficacy of medications intended for the lung are predicted by the CDS system 10 for a patient intubated and on the ventilator 12, in a case where the medications require specific ventilation modalities and techniques for maximal effectiveness. In another embodiment, local/regional/global dead space is computed by the CDS system 10 to change nebulizer treatment (nebulizer not shown) and patient position based on radiographic results and clinical assessment. In another embodiment, data fusion is computed by the CDS system 10 across radiographic imagery, physiologic, vent and monitoring data, assessment data to do multiple organ system modelling to determine optimum therapy plan for the patient including medication dosing, device settings, bed and patient orientation. In another embodiment, the CDS system 10 predicts change in gas flow dynamics to achieve best distribution for patient inhalation of medications. In another embodiment, closed loop to the ventilator 12 and the nebulizer is optimized by the CDS system 10 based on the physiological data and machine data.

Some other illustrative examples of using the CDS system 10 for prescriptive analytics follow. In one embodiment, the CDS system 10 is used for pre-selection of patients most likely to benefit from a therapy. For example, if a medication treats gram negative pneumonia, the CDS system 10 can calculate probability of patients on positive pressure ventilation and who are growing gram negative organisms in their sputum, worsening in the next 12 hours thus suitable for recommending initiating the new medication. Once the medication is ordered and administered, the CDS system 10 continues to recommend the optimal patient position for nebulized medication administration based on last chest X-ray defining the pulmonary lobes involved, and recommends the optimal vent settings for this patient, based on the cardiopulmonary model and known patient position (i.e. prone legs up). For example, combining patient demographic, genomics on a plurality of data, lab data, unvalidated and high fidelity data to propose the optimum therapy path for the patient including Cardiac medication, antibiotic medication, anti-coagulation medication, etc. In another embodiment, the CDS system 10 is used for pre-selection of therapy modalities based on medication administrations and/or orders.

The disclosure has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A clinical therapy system, comprising:
   a drug delivery device configured to deliver medication to a patient;
   one or more therapy devices configured to provide therapy to the patient;
   a computer comprising a local computer and a cloud computing resource, the computer being programmed to perform a CDS method including:
      receiving, with the local computer, clinical context data for the patient from a health information system (HIS);
      receiving, with the local computer, real time measurements for the patient from: (1) the drug delivery device, (2) one or more vital sign sensors, and (3) at least one device of the one or more therapy devices;
      generating, with the local computer and using the received real time measurements, coarse summary data for each of the: (1) drug delivery device; (2) the one or more vital sign sensors; and (3) at least one device of the one or more therapy devices, wherein coarse summary data comprises average, minimum, and maximum values at a coarser resolution than the real time measurements;
      communicating the generated coarse summary data from the local computer to the cloud computing resource;
      generating a clinical prediction for the patient based on a combination of the clinical context data and the real time measurements represented by the coarse summary data, wherein the clinical prediction is based on applying, with the cloud computing resource, one or more physiological models of body systems to the combination of the clinical context data and the real time measurements represented by the coarse summary data, wherein the one or more physiological models are derived by analyzing the real time measurements;
      outputting, via the computer, a therapy recommendation for the patient based on the clinical prediction for the patient; and
      controlling, via the computer, operation of the drug delivery device or one of the one or more therapy devices based on the therapy recommendation.

2. The system of claim 1, wherein the one or more therapy devices includes a ventilator and the receiving of the real time measurements includes receiving ventilator data from the ventilator; and
   the applying includes applying pulmonary and cardiac physiological models to the combination of the clinical context data and the real time measurements including the ventilator data to generate the clinical prediction for the patient.

3. The system of claim 2, wherein the ventilator data received from the ventilator includes pressure, volume, and fraction of inspired oxygen ($FiO_2$) data.

4. The system of claim 2, wherein the clinical prediction for the patient includes cardiac output, oxygen delivery pressure, flow and gas constituency settings for the ventilator; and
   the controlling includes increasing or decreasing an amount of pressure, flow and gas constituency settings from the ventilator delivered to the patient and increasing or decreasing an amount of a respiratory drug delivered to the patient by the drug delivery device.

5. The system of claim 1, wherein the one or more therapy devices includes a fluid regulatory device and the receiving of the real time measurements includes receiving fluid regulatory data from the fluid regulatory device; and
   the applying includes applying fluid and renal models to the combination of the clinical context data and the real time measurements including the fluid regulatory data to generate the clinical prediction for the patient.

6. The system of claim 5, wherein the clinical prediction for the patient includes intravenous fluid delivery dose amount and a delivery rate for the fluid regulatory device; and
   the controlling includes increasing or decreasing an amount of dose or a delivery rate from the fluid regulatory device delivered to the patient and increasing or decreasing an amount of a respiratory regulatory drug delivered to the patient by the drug delivery device.

7. The system of claim 1 wherein the one or more therapy devices includes a cooling blanket and the receiving of the real time measurements includes receiving patient temperature and thermal regulation data from the cooling blanket;
   the applying includes applying a patient temperature and a thermal regulation model to the combination of the clinical context data and the real time measurements including the patient temperature and thermal regulation data to generate the clinical prediction for the patient; and
   the controlling includes increasing or decreasing an amount of heat delivered to the patient from the cooling blanket.

8. The system of claim 1, wherein the one or more therapy devices includes a ventricular assist device and the receiving of the real time measurements includes receiving cardiac support data from the ventricular assist device;

the applying includes applying the cardiac model to the combination of the clinical context data and the real time measurements including the cardiac support data to generate the clinical prediction for the patient; and the controlling includes increasing or decreasing a speed of the ventricular assist device.

9. The system of claim 1, wherein the one or more therapy devices includes a mechanically adjustable patient bed and the receiving of the real time measurements includes receiving patient position data from the mechanically adjustable patient bed;

the applying includes applying a patient position model to the combination of the clinical context data and the real time measurements including the patient position data to generate the clinical prediction for the patient; and the controlling includes moving a portion of the mechanically adjustable patient bed to adjust a position of the patient.

10. The system of claim 1, wherein:

the receiving of the real time measurements for the patient includes receiving one or more of ECG data, pulse wave time of flight data, blood pressure data, pulse pressure variability data, and capnogram data from the one or more vital sign sensors providing monitoring of the patient; and the applying includes applying the one or more physiological models to the combination of the clinical context data and the real time measurements to generate a medication dosing recommendation for administering a medication to the patient.

11. The system of claim 10, wherein the outputting of the therapy recommendation for the patient includes outputting the medication dosing recommendation as a control signal to a drug delivery device to cause the drug delivery device to administer the medication to the patient in accord with the medication dosing recommendation.

12. The system of claim 11, wherein the CDS method further includes continuing to perform the receiving of clinical context data, the receiving of real time measurements, and the applying of the one or more physiological models of body systems during the administration of the medication to the patient to update the medication dosing recommendation for the patient during the administration of the medication to the patient.

13. The system of claim 1 wherein the clinical context data for the patient received from the HIS includes one or more of laboratory data, arterial blood gas (ABG) data, micro biology data, clinical assessments, procedure reports, and radiology and imaging results.

14. The system of claim 1, wherein the CDS method includes controlling operation of the drug delivery device and one of the one or more therapy devices based on the therapy recommendation.

15. The system of claim 1, wherein the therapy recommendation comprises a risk score of a worsening condition based on the medication delivered to the patient or the therapy provided to the patient.

16. A non-transitory computer readable medium storing instructions executable by at least one electronic processor of a computer system to perform a clinical decision support method, the method comprising:

receiving, via a local computer of the computer system, clinical context data for a patient from a health information system (HIS);

receiving, via the local computer of the computer system, real time measurements for the patient from: (1) a drug delivery device, (2) one or more vital sign sensors, and (3) at least one device of one or more therapy devices configured to provide therapy to the patient;

generating, via the local computer of the computer system, with the real time measurements, coarse summary data for each of the: (1) drug delivery device; (2) the one or more vital sign sensors; and (3) at least one device of the one or more therapy devices, coarse summary data comprising average, minimum, or maximum values at a coarser resolution than the real time measurements;

deriving, via a cloud computing resource of the computer system, one or more physiological models of body systems for the patient based on an analysis of the received real time measurements;

applying, via the cloud computing resource of the computer system, the one or more physiological models of body systems to a combination of the clinical context data and the real time measurements represented by the coarse summary data to generate a clinical prediction for the patient;

outputting, via the local computer of the computer system, a therapy recommendation for the patient based on the clinical prediction for the patient; and controlling, via the local computer of the computer system, operation of the drug delivery device or one of the one or more therapy devices based on the therapy recommendation.

\* \* \* \* \*